US012064248B2

(12) United States Patent
Lim

(10) Patent No.: US 12,064,248 B2
(45) Date of Patent: Aug. 20, 2024

(54) SYSTEM AND METHOD FOR DETERMINING DRIVER'S FATIGUE

(71) Applicant: HYUNDAI MOBIS CO., LTD., Seoul (KR)

(72) Inventor: Hyun Jun Lim, Uiwang-si (KR)

(73) Assignee: HYUNDAI MOBIS CO., LTD., Seoul (KR)

(*) Notice: Subject to any disclaimer, the term of this patent is extended or adjusted under 35 U.S.C. 154(b) by 221 days.

(21) Appl. No.: 17/735,809

(22) Filed: May 3, 2022

(65) Prior Publication Data

US 2022/0369978 A1 Nov. 24, 2022

(30) Foreign Application Priority Data

May 18, 2021 (KR) ........................ 10-2021-0064096

(51) Int. Cl.
| | | |
|---|---|---|
| *A61B 5/18* | (2006.01) | |
| *A61B 5/31* | (2021.01) | |
| *A61B 5/369* | (2021.01) | |
| *B60H 1/00* | (2006.01) | |
| *B60K 26/02* | (2006.01) | |
| *B60N 2/90* | (2018.01) | |
| *B60Q 9/00* | (2006.01) | |
| *B60S 1/08* | (2006.01) | |

(52) U.S. Cl.
CPC ............... *A61B 5/18* (2013.01); *A61B 5/31* (2021.01); *A61B 5/369* (2021.01); *B60H 1/008* (2013.01); *B60H 1/00835* (2013.01); *B60K 26/021* (2013.01); *B60N 2/976* (2018.02); *B60Q 9/00* (2013.01); *B60S 1/0818* (2013.01); *A61B 2503/22* (2013.01)

(58) Field of Classification Search
CPC .. A61B 5/18; A61B 5/31; A61B 5/372; A61B 5/369; A61B 5/291; A61B 2503/22; B60H 1/008; B60H 1/00835; B60H 1/00849; B60K 26/021; B60K 2360/74; B60K 35/00; B60K 35/65; B60K 35/654; B60K 28/06; B60N 2/976; B60Q 9/00; B60Q 1/1423; B60Q 1/02; B60Q 2300/314; B60Q 2300/321; B60S 1/0818; B60W 40/08; B60W 30/12; B60W 50/14; B60W 2040/0872; B60W 2050/0052; B60W 2050/0057; B60W 2050/143; B60W 2540/10; B60W 2540/22; B60W 2540/221; B60W 2552/50; B60W 2555/20; B60Y 2300/12
USPC ................................. 701/36, 39, 43, 45, 48
See application file for complete search history.

(56) References Cited

U.S. PATENT DOCUMENTS 11,832,946 B2 * 12/2023 Chou ..................... B60K 35/10

FOREIGN PATENT DOCUMENTS

| CN | 203192177 | * | 9/2013 | ............ B60W 40/08 |
|---|---|---|---|---|
| CN | 106073770 | * | 11/2016 | ............ A61B 5/746 |
| CN | 106394402 | * | 2/2017 | ............ B60Q 9/00 |
| CN | 106529421 | * | 3/2017 | ............ G06F 3/01 |
| CN | 106952448 | * | 7/2017 | ............ G08B 21/06 |

(Continued)

*Primary Examiner* — Hai H Huynh
(74) *Attorney, Agent, or Firm* — NovoTechIP International PLLC

(57) ABSTRACT

Proposed is system and method for determining a driver's fatigue to promote safe driving by determining the driver's fatigue according to a change in a brain wave of a driver during driving of a vehicle.

21 Claims, 3 Drawing Sheets

(56) References Cited

FOREIGN PATENT DOCUMENTS

| | | | | | |
|---|---|---|---|---|---|
| CN | 114005250 | * | 2/2022 | ............ | B60W 40/08 |
| CN | 114435372 | * | 5/2022 | ............ | B60W 40/08 |
| CN | 114435373 | * | 5/2022 | ............ | B60W 40/08 |
| KR | 10-2017-0049997 A | | 5/2017 | | |
| TW | 1824833 | * | 12/2023 | ............ | B60W 40/09 |

* cited by examiner

FIG. 2

| Types of brain waves | Frequency band | Form of brain waves | State of brain waves |
|---|---|---|---|
| Delta | 0.5~4 Hz | | State of deep sleep |
| Theta | 4~7 Hz | | States of being drowsy, distracted, and daydreamed |
| Alpha | 8~12 Hz | | State of loosened external concentration in relaxed state |
| SMR(Sensory Motor Rhythm) | 12~15 Hz | | State of maintaining concentration in state without moving |
| Beta | 15~18 Hz | | State of thinking and maintaining concentration in active state |
| High Beta | at least 18 Hz | | State of tension and anxiety |

SYSTEM AND METHOD FOR DETERMINING DRIVER'S FATIGUE

CROSS-REFERENCE TO RELATED APPLICATIONS

The present application claims priority to Korean Patent Application No. 10-2021-0064096, filed May 18, 2021, the entire contents of which is incorporated herein for all purposes by this reference.

BACKGROUND

1. Technical Field

The present invention relates to system and method for determining a driver's fatigue and, more particularly, to system and method for determining a driver's fatigue to promote safe driving by determining the driver's fatigue according to a change in a brain wave of the driver during driving of a vehicle.

2. Discussion of Related Art

Recently, various devices for improving conveniences of occupants in addition to a driving function when a vehicle is driven have been proposed.

For example, there are various devices for improving the conveniences such as a ventilated seat that allows cooling and heating air to be discharged from the seat cushion and seatback, a massage seat that implements a massage function from the seat cushion and seatback, an air conditioning filter that provides clean air to a vehicle interior by filtering external fine dust, and the like.

However, during long-distance driving, the driver's concentration is lowered, whereby driving safety is affected. In particular, when the driver's visual attention is reduced, normal driving becomes impossible, and thus a driving accident occurs.

The foregoing is intended merely to aid in the understanding of the background of the present invention and should not be taken as acknowledging that the present invention corresponds to the related art already known to those of ordinary skill in the art.

SUMMARY

Accordingly, the present invention has been made keeping in mind the above problems occurring in the related art, and an objective of the present invention is to provide system and method for determining a driver's fatigue to promote safe driving by determining the driver's fatigue according to a change in a brain wave of a driver during driving of a vehicle.

In order to achieve the above objective, according to one aspect of the present invention, there may be provided a system for determining a driver's fatigue, the system including: a brain wave detection unit configured to detect a brain wave of the driver; an initial value input unit configured to store an initial value of the brain wave of the driver; a brain wave comparison unit configured to compare a stored initial value of the brain wave with a change in the brain wave of the driver and to check whether the brain wave of the driver is changed and included in a preset brain wave range; and a controller configured to allow safety control to be performed, when the brain wave of the driver is included in the preset brain wave range.

The brain wave detection unit may receive the brain wave of the driver, which may be input from a brain wave determining device that detects brain wave information through a posterior parietal lobe of the driver.

The initial value input unit may transmit a message according to storage of the initial value of the brain wave to the driver, and when the driver permits the storage of the initial value of the brain wave, the initial value input unit stores the initial value of the brain wave according to a current brain wave of the driver.

The system may further include a filtering unit configured to filter the brain wave of the driver detected through the brain wave detection unit and to derive a power spectrum for a frequency band of a brain wave signal.

When the brain wave of the driver is included in the preset brain wave range, the controller may cause the safety control of generating a warning light or a warning sound to be performed.

When the brain wave of the driver is included in the preset brain wave range, the controller may cause the safety control of operating a massage function of the seat on which the driver is seated to be performed.

When the brain wave of the driver is included in the preset brain wave range, the controller may cause the safety control of reducing sensitivity of an accelerator pedal to be performed.

The system may further include: an indoor environment detection unit configured to detect an indoor carbon dioxide concentration and an indoor oxygen concentration, wherein, when the brain wave of the driver is included in the preset brain wave range, the controller may receive information according to the indoor carbon dioxide concentration and the indoor oxygen concentration through the indoor environment detection unit and cause the safety control of adjusting an introduction of outdoor air according to the indoor carbon dioxide concentration or the indoor oxygen concentration to be performed.

The system may further include: an outdoor environment detection unit configured to collect information according to a distance from an external obstacle or departure from a lane or not, wherein, when the brain wave of the driver is included in the preset brain wave range, the controller may receive information according to the distance from the external obstacle and the departure from the lane or not through the outdoor environment detection unit, and according to the distance from the external obstacle and the departure from the lane or not, the controller may cause the safety control of controlling vehicle driving of increasing the distance between the vehicle and the obstacle or preventing the vehicle from departing from the lane to be performed.

The system may further include: a weather detection unit configured to collect information according to a weather environment, wherein, when the brain wave of the driver is included in the preset brain wave range, the controller may receive information according to the weather environment through the weather detection unit.

When the weather environment is adverse due to snow or rain, the controller may cause a lamp to be driven and a wiper to be operated.

When a forward view is not secured such as at night or in fog, the controller may cause the lamp to be driven.

On the other hand, according to one aspect of the present invention, there may be provided a method for determining a driver's fatigue, the method including: a brain wave detecting step of detecting a brain wave of the driver; an initial value inputting step of storing an initial value of the brain wave of the driver; a brain wave comparing step of comparing a stored initial value of the brain wave with a change in the brain wave of the driver and of checking whether the brain wave of a driver is changed and included in a preset brain wave range; and a controlling step of performing safety control, when the brain wave of the driver is included in the preset brain wave range.

In the initial value inputting step, a message according to storage of the initial value of the brain wave may be transmitted to the driver, and when the driver permits the storage of the initial value of the brain wave, the initial value of the brain wave according to the current brain wave of the driver may be stored.

The method may further include a filtering step of filtering the brain wave of a driver detected through the detecting a brain wave and of deriving a power spectrum for a frequency band of a brain wave signal.

When the brain wave of the driver is included in the preset brain wave range, the safety control of generating a warning light or a warning sound may be performed in the controlling step.

When the brain wave of the driver is included in the preset brain wave range, the safety control of operating a massage function of the seat on which the driver is seated may be performed in the controlling step.

When the brain wave of the driver is included in the preset brain wave range, the safety control of reducing sensitivity of an accelerator pedal may be performed in the controlling step.

The method may further include: an indoor environment detecting step of detecting an indoor carbon dioxide concentration and an indoor oxygen concentration, wherein, when the brain wave of the driver is included in the preset brain wave range, in the controlling step, information according to the indoor carbon dioxide concentration and the indoor oxygen concentration may be received through the indoor environment detection unit, and the safety control of adjusting an introduction of outdoor air according to the indoor carbon dioxide concentration or the indoor oxygen concentration may be performed.

The method may further include: an outdoor environment detecting step of collecting information according to a distance from an external obstacle or departure from a lane or not, wherein, when the brain wave of the driver is included in the preset brain wave range, in the controlling step, information according to the distance from the external obstacle and the departure from the lane or not may be received through the outdoor environment detection unit, and according to the distance from the external obstacle and the departure from the lane or not, the safety control of controlling vehicle driving of increasing the distance between the vehicle and the obstacle or preventing the vehicle from departing from the lane may be performed.

The method may further include: a weather detecting step of collecting information according to a weather environment, wherein, when the brain wave of the driver is included in the preset brain wave range, information according to the weather environment may be received through the weather detection unit in the controlling step.

When the weather environment is adverse due to snow or rain, a lamp may be driven and a wiper may be operated in the controlling step.

When a forward view is not secured such as at night or in fog, the lamp may be driven in the controlling step.

The system and method for determining a driver's fatigue having a structure as described above can promote safe driving by determining a driver's fatigue according to a change in a brain wave of the driver during driving of a vehicle.

BRIEF DESCRIPTION OF THE DRAWINGS

The above and other objectives, features, and other advantages of the present invention will be more clearly understood from the following detailed description when taken in conjunction with the accompanying drawings, in which:

FIG. 2 is a view explaining a state according to waveforms of brain waves.

DETAILED DESCRIPTION

Figure 1:
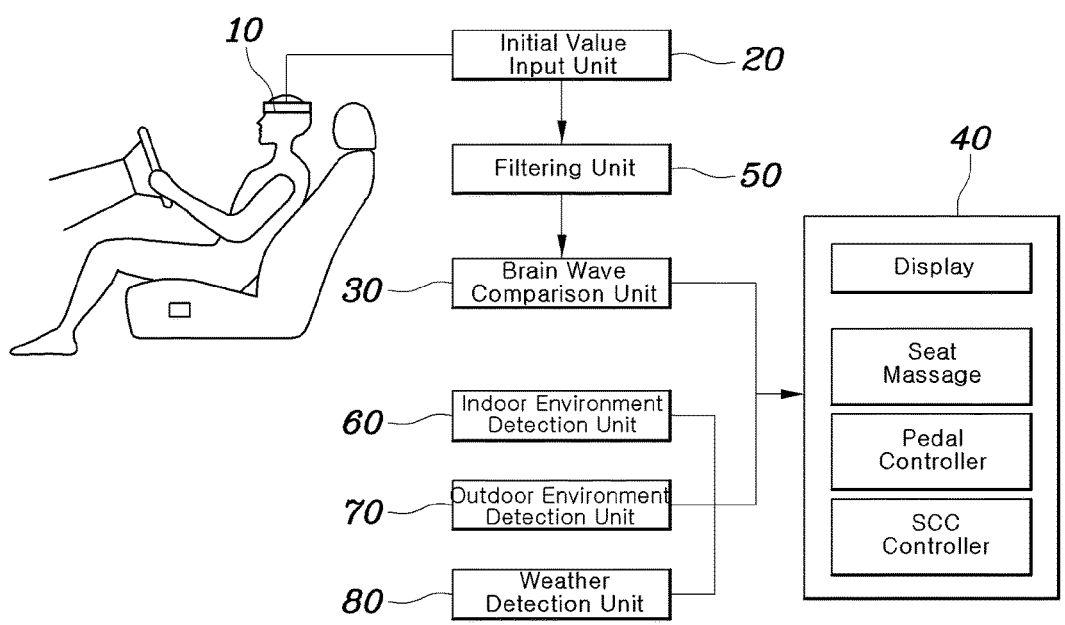
FIG. 1 is a block diagram of a system for determining a driver's fatigue according to the present invention.
Figure 3:
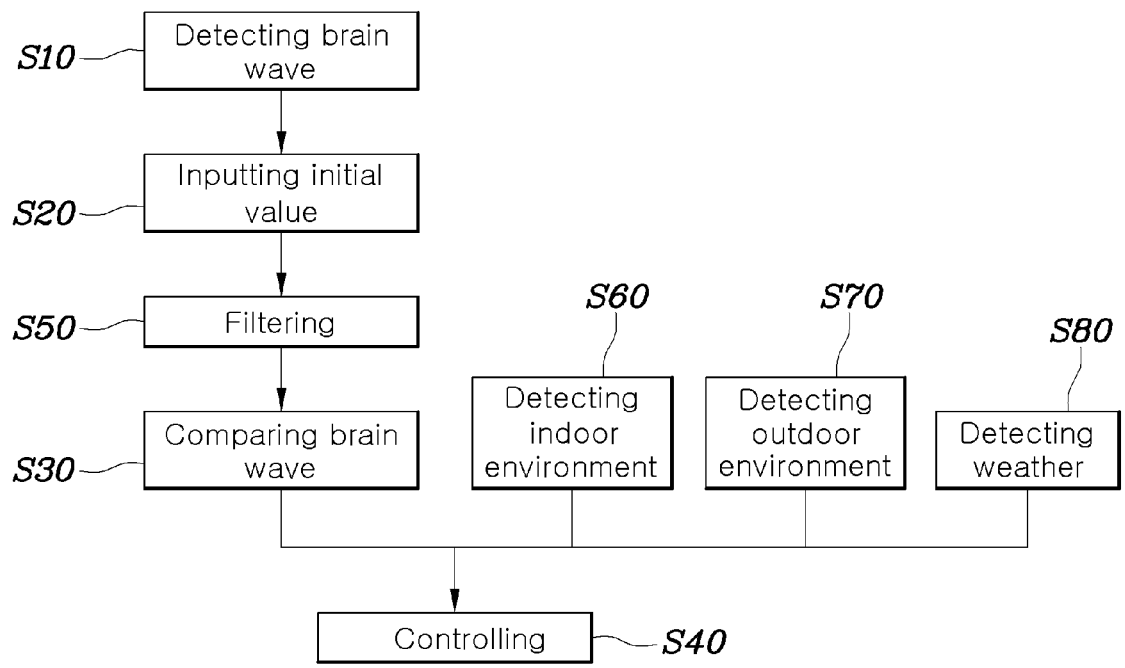
FIG. 3 is a flowchart of a method for determining the driver's fatigue according to the present invention.

Hereinbelow, the system and method for determining a driver's fatigue according to exemplary embodiments of the present invention will be described in detail with reference to the accompanying drawings. FIG. 1 is a block diagram of a system for determining a driver's fatigue according to the present invention, FIG. 2 is a view explaining a state according to waveforms of brain waves, and FIG. 3 is a flowchart of a method for determining a driver's fatigue according to the present invention.

As shown in FIG. 1, the system for determining a driver's fatigue according to the present invention includes: a brain wave detection unit 10 configured to detect a brain wave of a driver; an initial value input unit 20 configured to store an initial value of the brain wave of a driver; a brain wave comparison unit 30 (or a brain wave comparator) configured to compare a stored initial value of the brain wave with a change in the brain wave of a driver and to check or determine whether the brain wave of a driver is changed and included in a preset brain wave range; and a controller 40 configured to allow safety control to be performed, when the brain wave of a driver is included in the preset brain wave range.

The brain wave detection unit 10 outputs a brain wave signal corresponding to the brain wave. The brain wave detection unit 10 may receive the brain wave of a driver, which is input from a brain wave measuring device that detects brain wave information through a posterior parietal lobe of the driver. That is, the posterior parietal lobe is responsible for processing visual information and concentration, and the brain wave detection unit 10 may detect the driver's visual concentration of attention through a brain wave signal analysis in the posterior parietal lobe. Here, the brain wave measuring device may be configured as a headset or a headband type that is provided on the seat.

The initial value input unit 20, which sets a reference value for detecting the driver's state according to the change in the brain wave, stores the initial value of the brain wave of a driver while the driver is seated on the seat.

Specifically, the initial value input unit 20 may store the brain wave of a driver, the brain wave being detected through the brain wave detection unit 10 when the driver sits on the seat or wears the brain wave measuring device, as an initial value.

That is, when the driver first sits on the seat or wears the brain wave measuring device, a state of the brain wave of a driver may be determined to be normal, thus the brain wave of a driver, detected through the brain wave detection unit 10 when the driver sits on the seat or wears the brain wave measuring device, is stored as an initial value.

Meanwhile, the initial value input unit 20 may transmit a message according to storage of the initial value of the brain wave to the driver, and when the driver permits the storage of the initial value of the brain wave, the initial value input unit 20 may store the initial value of the brain wave according to a current brain wave of the driver.

In this way, the initial value input unit 20 transmits the message according to the storage of an initial value of the brain wave to the driver when storing the initial value according to the brain wave of a driver, thereby allowing the driver to recognize the storage of the initial value of the brain wave.

For example, when the brain wave is stored as an initial value in a state the brain wave of a driver is unstable due to a movement or emotional change of the driver before boarding the vehicle, accurate control according to the brain wave may not be performed. Accordingly, the initial value input unit 20 transmits a message according to the storage of the initial value of the brain wave to the driver through the display when storing the initial value of the brain wave according to the brain wave of a driver, and when the driver permits storing the initial value of the brain wave in a state his or her brain wave is stabilized, the initial value of the brain wave according to the current brain wave of a driver is allowed to be stored.

On the other hand, the brain wave comparison unit 30 compares the initial value of the brain wave stored in the initial value input unit 20 with the change in the brain wave of a driver detected by the brain wave detection unit 10 and checks or determines whether the brain wave of a driver that is changed is included in a preset brain wave range.

That is, the brain wave comparison unit 30 may detect a change in the driver's visual concentration of attention according to the change in the brain wave of a driver on the basis of the medical database. In addition, in the case of the brain wave, it serves as a basis for determining a driver's condition according to various waveforms, so the brain wave comparison unit 30 may determine the driver's condition according to each waveform of the brain wave.

To this end, the system may further include a filtering unit 50 configured to filter the brain wave of a driver detected through the brain wave detection unit 10 and to derive a power spectrum for a frequency band of a brain wave signal.

Such a filtering unit 50 may remove noise included in the brain wave signal measured for the brain wave of a driver detected through the brain wave detection unit 10 using filters such as a low pass filter, a notch filter, and the like. Here, the noise may include noise generated by blinking, AC power noise, and DC drift components as well as factors that interfere with extraction of brain wave feature points. In this way, the filtering unit 50 may extract the pre-processed brain wave signal through the pre-processing step.

In addition, the filtering unit 50 extracts the feature points by using the pre-processed brain wave signal. Here, the extraction of the feature points may be performed through frequency power spectrum analysis through Fourier Transform (FT) or Fast Fourier Transform (FFT), Short Time Fourier Transform (STFT), or the like. That is, the power spectrum density (PSD) may be calculated for theta wave (4-7 Hz), alpha wave (8-12 Hz), SMR wave (12-15 Hz), and beta wave (15-18 Hz), which are highly related to the concentration of attention according to the frequency band of the brain wave signal, thereby extracting the feature points regarding the size by each band.

That is, as shown in FIG. 2, the filtering unit 50 derives a power spectrum according to the frequency band of the brain wave, and the brain wave comparison unit 30 compares the change in the power spectrum according to the change in each brain wave with the initial value of the brain wave and checks or determines whether the waveform of the brain wave of a driver is included in the preset brain wave range according to the feature points related to the size by each preset band.

Through this, the brain wave comparison unit 30 may determine whether the frequency band of each brain wave signal is included in the preset brain wave range and, when the brain wave of a driver is included in the preset brain wave range, allows the controller 40 to perform the safety control.

Here, the safety control of the controller 40 may include message delivery, convenience devices, and vehicle control.

In one embodiment, when the brain wave of a driver is included in the preset brain wave range, the controller 40 allows the safety control of generating a warning light or a warning sound to be performed.

That is, the controller 40 may transmit a danger signal according to the change in the brain wave through a display provided in the vehicle or may transmit a danger signal according to the change in the brain wave through a speaker. Due to this, the driver may check the transmitted message, thereby recovering concentration.

In another embodiment, when the brain wave of a driver is included in the preset brain wave range, the controller 40 allows the safety control of operating a massaging function of the seat on which the driver is seated to be performed.

In this way, a massage device provided on the seat may be operated to massage the driver, thereby stimulating the driver's blood circulation to relieve the fatigue and enabling the reduced concentration to be restored through the massage.

In another embodiment, when the brain wave of a driver is included in the preset brain wave range, the controller 40 allows the safety control of reducing sensitivity of the accelerator pedal to be performed.

In this way, when the brain wave of a driver is included in the preset brain wave range, the driver's driving concentration is lowered, so, by adjusting the sensitivity of the accelerator pedal to be reduced, an accident caused by maloperation of the accelerator pedal may be prevented.

Meanwhile, the controller 40 may perform the safety control according to an indoor environment along with the brain wave of a driver.

Accordingly, the system may further include an indoor environment detection unit 60 configured to detect an indoor carbon dioxide concentration and an indoor oxygen concentration. Such an indoor environment detection unit 60 collects information according to the carbon dioxide concentration and the indoor oxygen concentration through a carbon dioxide sensor or an oxygen sensor provided in a cabin and transmits the corresponding information to the controller 40.

When the brain wave of a driver is included in (or within) the preset brain wave range, the controller 40 receives information according to the indoor carbon dioxide concentration and oxygen concentration through the indoor environment detection unit 60 and allows the safety control of adjusting an introduction of outdoor air according to the indoor carbon dioxide concentration or oxygen concentration to be performed.

That is, when the carbon dioxide concentration is high or the oxygen concentration is low in the cabin, it causes fatigue to the driver, so the controller 40 allows outside air to be introduced into the cabin, when the carbon dioxide concentration is high or the oxygen concentration is low in a state the brain wave of a driver is included in the preset brain wave range, thereby improving the driver's fatigue by the clean air being supplied to the cabin.

On the other hand, the system may further include an outdoor environment detection unit 70 configured to collect information according to a distance from an external obstacle or departure from a lane or not. Such an outdoor environment detection unit 70 may be a camera, radar, or lidar.

When the brain wave of a driver is included in the preset brain wave range, the controller 40 receives information according to the distance from the external obstacle and the departure from the lane or not through the outdoor environment detection unit 70 and, according to the distance from the external obstacle and the departure from the lane or not, may allow the safety control of controlling vehicle driving of increasing the distance between the vehicle and the obstacle or preventing the vehicle from departing from the lane to be performed.

That is, in a state the driver's concentration is reduced as the brain wave of a driver is included in the preset brain wave range, and when the vehicle approaches an external obstacle or deviates from the lane, the driver may not recognize this, and thus a vehicle crash accident may occur.

Accordingly, when awareness of a risk of an accident is low due to a decrease in the driver's concentration, the controller 40 allows relatively stable autonomous driving to be performed rather than unstable driver's driving, thereby preventing a safety accident from occurring.

Each safety control of the controller 40 according to that the above-described brain wave of a driver is included in the preset brain wave range may be selectively performed according to the wavelength of the brain wave, and each embodiment may be performed in a complex manner according to the driver's condition.

On the other hand, the system may further include a weather detection unit 80 configured to collect information according to a weather environment, wherein, when the brain wave of a driver is included in the preset brain wave range, the controller 40 receives information according to the weather environment through the weather detection unit 80.

The weather detection unit 80 may collect information according to the weather environment through satellite communication, wherein, when the brain wave of a driver is included in the preset brain wave range, the controller 40 takes into consideration the influence of the driver according to the weather environment.

Specifically, when the weather environment is adverse due to snow or rain, the controller 40 causes a lamp to be driven and a wiper to be operated.

In addition, when a forward view is not secured such as at night or in fog, the controller 40 causes the lamp to be driven.

That is, when the brain wave of a driver is included in the preset brain wave range, the controller 40 allows the lamp and the wiper to be operated in response to adverse conditions caused by snow or rain, thereby allowing the driver to recognize the adverse weather conditions. As a result, the driver may focus on driving by regaining concentration.

In addition, the controller 40 may enable the driver to secure a forward view and focus on driving by causing the lamp to be driven when a forward view is not secured such as at night or in fog.

On the other hand, as shown in FIG. 3, a method for determining a driver's fatigue includes: a brain wave detecting step S10 of detecting a brain wave of a driver; an initial value inputting step S20 of storing an initial value of the brain wave of a driver; a brain wave comparing step S30 of comparing a stored initial value of the brain wave with a change in the brain wave of a driver and of confirming whether the brain wave of a driver that is changed and included in a preset brain wave range; and a controlling step S40 of performing safety control, when the brain wave of a driver is included in the preset brain wave range.

In the brain wave detecting step S10, the brain wave of a driver received from a brain wave determining device that measures brain wave information through the posterior parietal lobe of the driver may be input.

Meanwhile, in the initial value inputting step S20, a message according to storage of the initial value of the brain wave may be transmitted to the driver and, when the driver permits the storage of the initial value of the brain wave, the initial value of the brain wave according to the current brain wave of a driver may be stored.

As such, in the initial value inputting step S20, the message according to the storage of the initial value of the brain wave may be transmitted to the driver when storing the initial value according to the brain wave of a driver, thereby enabling the driver to recognize the storage of the initial value of the brain wave.

On the other hand, the method may further include a filtering step S50 of filtering the brain wave of a driver detected through the brain wave detecting step S10 and of deriving a power spectrum for a frequency band of a brain wave signal.

Through this, noise included in the brain wave detected in the brain wave detecting step S10 is filtered, and the brain wave wavelength may be extracted by each band using the pre-processed brain wave signal.

Meanwhile, when the brain wave of a driver is included in a preset brain wave range, in the controlling step S40, the safety control of generating a warning light or a warning sound may be performed.

That is, in the controlling step S40, a danger signal according to a change in the brain wave may be transmitted through a display provided in a vehicle, or a danger signal according to a change in a brain wave may be transmitted through a speaker.

In addition, when the brain wave of a driver is included in the preset brain wave range, in the controlling step S40, the safety control of operating a massaging function of the seat on which the driver is seated may be performed.

That is, in the controlling step S40, a massage device provided on the seat may be allowed to be operated so that massage is provided to the driver, thereby stimulating the driver's blood circulation to relieve the fatigue and enabling the reduced concentration to be restored through the massage.

In addition, when the brain wave of a driver is included in the preset brain wave range, in the controlling step S40, the safety control of reducing sensitivity of the accelerator pedal may be performed.

As such, in the controlling step S40, when the brain wave of a driver is included in the preset brain wave range, the driver's driving concentration is lowered, so, by adjusting the sensitivity of the accelerator pedal to be reduced, an accident caused by maloperation of the accelerator pedal may be prevented.

On the other hand, the method may further include an indoor environment detecting step S60 of detecting an indoor carbon dioxide concentration and an indoor oxygen concentration, wherein, when the brain wave of a driver is included in the preset brain wave range, in the controlling step S40, information according to the indoor carbon dioxide concentration and oxygen concentration is received through the indoor environment detection unit 60, and the safety control of adjusting an introduction of outdoor air according to the indoor carbon dioxide concentration or oxygen concentration is performed.

That is, when the carbon dioxide concentration is high or the oxygen concentration is low in a cabin, it causes fatigue to the driver, so, in the controlling step S40, outside air is allowed to be introduced into the cabin, when the carbon dioxide concentration is high or the oxygen concentration is low in a state the brain wave of a driver is included in the preset brain wave range, thereby improving the driver's fatigue by the clean air being supplied to the cabin.

On the other hand, the method may further include an outdoor environment detecting step S70 of collecting information according to a distance from an external obstacle or departure from a lane or not, wherein, when the brain wave of a driver is included in the preset brain wave range, in the controlling step S40, information according to the distance from the external obstacle and the departure from the lane or not is received through the outdoor environment detection unit 70, and according to the distance from the external obstacle and the departure from the lane or not, vehicle control of increasing the distance between the vehicle and the obstacle or preventing the vehicle from departing from the lane is performed.

That is, in a state the driver's concentration is reduced as the brain wave of a driver is included in the preset brain wave range, and when the vehicle approaches an external obstacle or deviates from the lane, the driver may not recognize this, and thus a vehicle crash accident may occur.

Accordingly, when awareness of a risk of an accident is low due to a decrease in the driver's concentration, in the controlling step S40, relatively stable autonomous driving is performed rather than unstable driver's driving.

On the other hand, the method may further include a weather detecting step S80 of collecting information according to a weather environment, wherein, when the brain wave of a driver is included in the preset brain wave range, in the controlling step S40, information according to the weather environment is received through the weather detection unit 80.

That is, when the weather environment is adverse due to snow or rain, in the controlling step S40, a lamp is driven and a wiper is operated.

In addition, when a forward view is not secured such as at night or in fog, in the controlling step S40, the lamp is driven.

The system and method for determining a driver's fatigue having a structure as described above promotes safe driving by determining a driver's fatigue according to the change in the brain wave of the driver during driving of a vehicle.

Although the present invention has been shown and described in relation to specific embodiments, it will be obvious to those of ordinary skill in the art that the present invention may be variously improved and changed within a scope of not departing from the spirit of the present invention provided by the following claims.

What is claimed is:

1. A system for determining a driver's fatigue, comprising:
   a brain wave detection unit configured to detect a brain wave of a driver of a vehicle and generate a brain wave value based on the detected brain wave;
   an initial value input unit configured to store an initial brain wave value of the driver;
   a brain wave comparison unit configured to (1) determine whether the driver's brain wave has changed based on the initial brain wave value and the brain wave value and (2) detect whether the brain wave value is within a preset range; and
   a controller configured to perform a safety control of the vehicle when the brain wave value is within the preset range,
   wherein, to perform the safety control of the vehicle, the controller is configured to reduce a sensitivity of an accelerator pedal of the vehicle.

2. The system of claim 1, wherein the brain wave detection unit includes a brainwave data detection device configured to collect the driver's brain wave from the driver's a posterior parietal lobe of the driver.

3. The system of claim 1, wherein the initial value input unit is configured to:
   receive, from the driver, a permission to set the initial brain wave value; and
   in response to receiving the permission, determine the initial brain wave value based on a current brain wave of the driver.

4. The system of claim 1, further comprising a filtering unit configured to filter the detected driver's brain wave and derive, from the filtered driver's brain wave, a power spectrum for a frequency band of the driver's brain wave.

5. The system of claim 1, wherein the safety control performed by the controller includes causing a warning light or warning sound to be output.

6. The system of claim 1, wherein the safety control performed by the controller includes causing a seat of the vehicle to perform a massaging function.

7. The system of claim 1, further comprising an indoor environment detection unit configured to detect an indoor carbon dioxide concentration and an indoor oxygen concentration,
   wherein the safety control performed by the controller includes causing outdoor air to be introduced to a cabin of the vehicle based on the detected indoor carbon dioxide concentration or indoor oxygen concentration.

8. The system of claim 1, further comprising an outdoor environment detection unit configured to detect a distance between the vehicle and an external obstacle or a departure of the vehicle from a current lane,
   wherein the safety control performed by the controller includes causing the vehicle to slow down to increase the distance between the vehicle and the obstacle or preventing the vehicle from departing from the current lane.

9. The system of claim 1, further comprising a weather detection unit configured to collect weather information, wherein the controller is configured to receive the weather information from the weather detection unit.

10. The system of claim 9, wherein the safety control performed by the controller includes causing a lamp or wiper of the vehicle to be activated based on the collected weather information.

11. The system of claim 9, wherein the safety control performed by the controller includes causing a lamp of the vehicle to be activated when a forward view of the driver is not secured.

12. A method for determining a driver's fatigue, comprising:
- storing, at a data storage, an initial brain wave value of a driver of a vehicle;
- detecting a brain wave of the driver and generating a brain wave value based on the detected brain wave of the driver;
- determining whether the brain wave of the driver has changed based on the brain wave value and the initial brain wave value;
- determining whether the brain wave value is within a preset range; and
- in response to determining that the brain wave value is within the preset range, performing a safety control of the vehicle,
- wherein performing the safety control of the vehicle includes reducing a sensitivity of an accelerator pedal of the vehicle.

13. The method of claim 12, further comprising:
- receiving, from the driver, a permission to set the initial brain wave value; and
- in response to receiving the permission, detecting a current brain wave of the driver and setting the initial brain wave value based on the detected current brain wave.

14. The method of claim 12, further comprising filtering the brain wave of the driver and deriving, from the filtered brain wave of the driver, a power spectrum for a frequency band of the brain wave of the driver.

15. The method of claim 12, wherein performing the safety control includes causing a warning light or warning sound to be activated.

16. The method of claim 12, wherein performing the safety control includes causing a seat of the vehicle to perform a massaging function.

17. The method of claim 12, further comprising detecting an indoor carbon dioxide concentration and an indoor oxygen concentration,
- wherein performing the safety control includes causing outdoor air to be introduced to a cabin of the vehicle based on the detected indoor carbon dioxide concentration or indoor oxygen concentration.

18. The method of claim 12, further comprising detecting a distance between the vehicle and an external obstacle or detecting a departure of the vehicle from a current lane,
- wherein performing the safety control includes slowing down the vehicle to increase the distance between the vehicle and the external obstacle or preventing the vehicle from departing from the current lane.

19. The method of claim 12, further comprising collecting weather information.

20. The method of claim 19, wherein performing the safety control includes causing a lamp or wiper of the vehicle to be activated based on the collected weather information.

21. The method of claim 19, wherein performing the safety control includes causing a lamp of the vehicle to be activated when a forward view of the driver is not secured.

* * * * *